US009273227B2

(12) United States Patent
Freeman et al.

(10) Patent No.: US 9,273,227 B2
(45) Date of Patent: Mar. 1, 2016

(54) WATERBORNE AQUEOUS-ALCOHOL SOLUBLE PROTEIN COMPOSITIONS, APPLICATIONS, AND METHODS

(71) Applicant: POET RESEARCH, INC., Sioux Falls, SD (US)

(72) Inventors: Leif Sedgewick Freeman, Sioux Falls, SD (US); John Warrent Lawton, Jr., Sioux Falls, SD (US); Melvin Glenn Mitchell, Penrose, NC (US); Marvin Lynn Mitchell, Parker, CO (US); Laura Martin, Brookings, SD (US)

(73) Assignee: POET RESEARCH, INC., Sioux Falls, SD (US)

( * ) Notice: Subject to any disclaimer, the term of this patent is extended or adjusted under 35 U.S.C. 154(b) by 175 days.

(21) Appl. No.: 13/786,462

(22) Filed: Mar. 6, 2013

(65) Prior Publication Data

US 2014/0251180 A1    Sep. 11, 2014

(51) Int. Cl.

| C09D 189/00 | (2006.01) |
| C07K 1/14 | (2006.01) |
| D21H 19/12 | (2006.01) |
| C07K 14/425 | (2006.01) |
| C07K 14/47 | (2006.01) |
| C08K 5/10 | (2006.01) |
| C08L 89/00 | (2006.01) |
| C09J 189/00 | (2006.01) |
| C08J 3/05 | (2006.01) |

(52) U.S. Cl.
CPC ............. *C09D 189/00* (2013.01); *C07K 1/145* (2013.01); *C07K 14/425* (2013.01); *C07K 14/4732* (2013.01); *C08J 3/05* (2013.01); *C08K 5/10* (2013.01); *C08L 89/00* (2013.01); *C09J 189/00* (2013.01); *D21H 19/12* (2013.01); *C08J 2389/00* (2013.01)

(58) Field of Classification Search
None
See application file for complete search history.

(56) References Cited

U.S. PATENT DOCUMENTS

| 2,185,124 A | 12/1939 | Coleman |
| 2,360,081 A | 10/1940 | Stewart |
| 2,377,237 A | 5/1945 | James |
| 2,657,148 A | 10/1953 | Enrlich |
| 2,545,656 A | 3/1954 | Dunne |
| 2,810,656 A | 10/1957 | Mcdowell |
| 5,021,248 A | 6/1991 | Stark |
| 5,182,130 A | 1/1993 | Haralampu |
| 5,254,673 A | 10/1993 | Cook et al. |
| 5,260,396 A * | 11/1993 | Kroner et al. .................. 527/201 |
| 5,324,351 A | 6/1994 | Oshlack |
| 5,705,207 A * | 1/1998 | Cook .................. A21D 13/0012 426/56 |
| 7,737,200 B2 | 6/2010 | Jabar et al. |
| 8,795,760 B2 | 8/2014 | Lawton |
| 2013/0014673 A1* | 1/2013 | Freeman .............. C07K 14/425 106/161.1 |

FOREIGN PATENT DOCUMENTS

| WO | WO 2013/010119 | * | 1/2013 |
| WO | WO 2013/010119 A2 | | 1/2013 |

OTHER PUBLICATIONS

U.S. Appl. No. 13/548,839, filed Jan. 17, 2013, Freeman.
U.S. Appl. No. 12/965,255, filed Jun. 16, 2011, Lawton Jr., John.
U.S. Appl. No. 12/651,401, filed Jul. 15, 2010, Lawton Jr., John.
ISR for PCT/US2014/020942, date of completion: May 27, 2014.
Lawton, John W, "Zein: A History of Processing and Use", Cereal Chemistry, AACC International Inc., US, vol. 79, No. 1, Jan. 1.
Bietz et al. "Zein Composition in Hard and Soft Endosperm of Maize", Cereal Chemistry, vol. 70, No. 1, 1993, pp. 105-108.
Swallen, LC "Zein_A New Industrial Protein", Industrial and Engineering Chemistry, vol. 33, No. 3, Mar. 1941, pp. 394-398.
Esen, A,"Separation of Alcohol-Soluble Proteins (Zein) from Maize into Three Fractions by Differential Solubility",Plant Physiol.80: 1986, p. 623-27.
Esen, A,"A Proposed Nomenclature for the Alcohol-soluble Proteins (Zeins) of Maize (Zea mays L.)",J of Cereal Science 5:1987;p. 117-128.
Lawton, J. et al., "Chapter 9—Proteins of the Kernel", Corn: Chemistry and Technology, 2nd edition, (2003) p. 313-354.
Shewry, P. et al., "Review Article—The prolamin storage protein of cereal seeds: structure and evolution", Biocehm. J. 267: (1990) p. 1-12.

* cited by examiner

*Primary Examiner* — Melvin C Mayes
*Assistant Examiner* — Colette Nguyen
(74) *Attorney, Agent, or Firm* — Edna Vassilovski

(57) ABSTRACT

Waterborne aqueous-alcohol soluble protein compositions, methods of making the compositions, and applications thereof are disclosed. The dispersion compositions include protein, water, acid, and optionally an ester of a carboxylic acid. The methods of making the compositions including combining the protein, water, acid and optionally ester to form a dispersion without the benefit of alcohol. Applications include industrial and food applications, such as binders and coatings, for example paint binders or coatings for paper products and pharmaceuticals.

11 Claims, 6 Drawing Sheets

WATERBORNE AQUEOUS-ALCOHOL SOLUBLE PROTEIN COMPOSITIONS, APPLICATIONS, AND METHODS

FIELD

This specification relates to waterborne aqueous-alcohol soluble protein dispersions, for example waterborne aqueous-alcohol soluble waterborne dispersions which can be made without the benefit of alcohol. This specification also relates to methods of making the dispersions, and methods of using same. This specification also relates to dispersions comprising proteins derived from corn- or grain-to-ethanol conversion processes, for example proteins which are extracted from fermentation products of corn- or grain-to-ethanol conversion processes, and methods of making and using such dispersions.

BACKGROUND

Prolamins have many potential food and industrial uses. For example, at least some prolamins may be processed as coatings, binders, and/or adhesives and used in paper and/or pharmaceutical applications among other possibilities.

Barriers to the commercial use of prolamins include the high cost of producing prolamins, and the difficulty of maintaining prolamins in an aqueous environment. Prolamins are generally soluble in aqueous-alcohol solutions. However, the use of organic solvents, for example, in the preparation of polymer coating formulations is viewed as a disadvantage due to potential problems with flammability, carcinogenicity, and safety in use. Additionally, the use of organic solvents may not be favored due to environmental concerns.

SUMMARY

The present disclosure relates to waterborne aqueous-alcohol soluble protein compositions, methods of making such compositions, and applications of such compositions.

In some embodiments, the compositions include a solid portion and a liquid portion, in which the solid portion includes an aqueous-alcohol soluble protein, the liquid portion includes water and an acid, and the solid portion is dispersible in the liquid portion without the benefit of alcohol in the liquid portion. In further embodiments, the compositions also include an ester of a carboxylic acid. In some embodiments, the protein is derived from milk, derived from soy protein isolate, is a prolamin or may be combinations thereof. In some embodiments, the prolamin is a zein composition including at least one of beta-zeins or gamma-zeins, for example in at least a total amount sufficient for the solid portion to disperse in the liquid portion, for example the beta-zeins and gamma-zeins are together present in a total amount of at least 12% by mass of the total zein in the composition. In some embodiments, the amount and type of each component is chosen to result in a dispersion having a desired flowability and to result in the protein remaining dispersed for a desired period of time. In some embodiments, the protein is a zein and the amount of protein ranges from about 0.2% to about 34.6% by mass of the composition, the amount of water ranges from about 38.1% to about 99.6% by mass of the composition, the amount of acid ranges from about 0.4% to about 48.1% by mass of the composition, and the amount of ester ranges from about 0.0% to about 53.1% by mass of the composition.

In some embodiments, the compositions are made by a process which includes combining together an amount of water, an amount of an acid, an amount of an aqueous-alcohol soluble protein, and optionally an amount of an ester of a carboxylic acid to form a dispersion without the need for also adding an amount of an alcohol. In some embodiments, combining includes heating, stirring or both, simultaneously and/or sequentially, and wherein each of which can occur in one or more steps. In some embodiments, the process further includes drying the dispersion after it is formed. In some embodiments, the process further includes re-dispersing the dispersion after it is dried.

The disclosure also provides end-use applications of the compositions. In some embodiments, the end-use applications are products such as binders, glues, adhesives, sealants, and/or coatings. In some embodiments, the end-use applications are suitable for use in various industries, such as the paint and coatings industry, the architectural industry (interior and exterior), wood products industry (e.g. furniture, office, cabinets, wood flooring), food and industrial industry (e.g. containers and closures), the paper and plastic industries (e.g. as special substrates including binders and coatings), and the pharmaceutical industry (e.g. coatings).

The disclosure also provides methods of making waterborne aqueous-alcohol soluble protein compositions. In some embodiments, the methods include combining a set of components in one or more steps to form a dispersion without the need for the addition of alcohol (for example, without the addition of alcohol), wherein the components include an amount of an aqueous-alcohol soluble protein, an amount of water, an amount of an acid, and optionally an amount of an ester of a carboxylic acid. In some embodiments, the combining includes dissolving the acid in the water to form a first composition, and mixing the ester and the protein into the first composition to form the dispersion. In further embodiments, mixing involves stirring, heating and cooling. In some embodiments, combining involves dissolving ester and acid in water to form a first liquid portion; dissolving acid in water to form a second liquid portion; adding together the first liquid portion with the protein to form a first mixture; heating the second liquid portion; heating water; alternatively adding while stirring the heated second liquid portion and the heated water in one or more steps to the first mixture to form a second mixture of desired viscosity; and, cooling while stirring the second mixture to room temperature. In further embodiments, the methods involve drying the dispersion after it is formed. In yet further embodiments, the methods include re-dispersing the dried dispersion in water.

The disclosure also provides methods for using the waterborne aqueous-alcohol soluble protein compositions. In some embodiments, the methods involve preparing at least one of a binder or coating from the protein compositions. In yet other embodiments, the methods involve preparing a paint composition, a composition for use in pharmaceutical applications, a composition for use in food applications, a paper composition, a varnish composition, or an adhesive composition using the protein compositions.

The identified embodiments are exemplary only and are therefore non-limiting. The details of one or more non-limiting embodiments according to the disclosure are set forth in the accompanying drawings and the descriptions below. Other embodiments according to the disclosure should be apparent to those of ordinary skill in the art after consideration of the present disclosure.

DETAILED DESCRIPTION

I. Definitions

Figure 1:
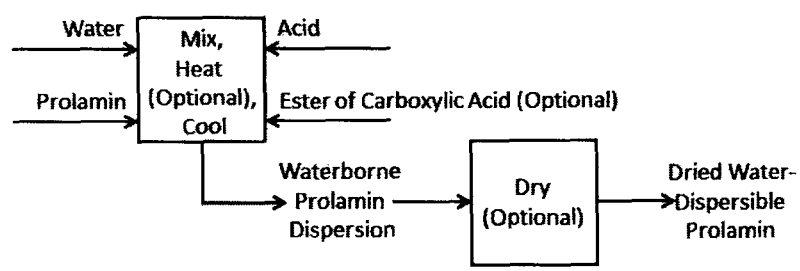
FIG. 1 is a flow diagram of an embodiment of making waterborne aqueous-alcohol soluble protein dispersions in accordance with this disclosure.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Where ever the phrases "for example," "such as," "including" and the like are used herein, the phrase "and without limitation" is understood to follow unless explicitly stated otherwise.

The terms "comprising" and "including" and "involving" (and similarly "comprises" and "includes" and "involves") are used interchangeably and mean the same thing. Specifically, each of the terms is defined consistent with the common United States patent law definition of "comprising" and is therefore interpreted to be an open term meaning "at least the following" and also interpreted not to exclude additional features, limitations, aspects, etc.

The term "about" is meant to account for variations due to experimental error or to permit deviations from the measurements that don't negatively impact the intended purpose. The term "substantially" is meant to permit deviations from the descriptive term that don't negatively impact the intended purpose. All measurements or numbers are implicitly understood to be modified by the word about, even if the measurement or number is not explicitly modified by the word about. All descriptive terms are implicitly understood to be modified by the word substantially, even if the descriptive term is not explicitly modified by the word substantially.

Where ever the terms "a" or "an" are used, "one or more" is understood unless explicitly stated otherwise or such interpretation is nonsensical in context. For example, "comprising a prolamin" means "comprising one or more (types) of prolamins."

The term "dispersion," when used to describe a chemical composition, is given the broadest possible meaning and encompasses but is not limited to solutions, emulsions, colloids, coarse dispersions (suspensions).

The term "zein," as used herein unless explicitly stated otherwise or non-sensical in context means "zein composition." More specifically, the term "zein" means zein compositions comprising one or more forms of zein. For example, zein extracted from fermentation products of a corn dry milling process comprises a combination of several forms of zein, and is suitable for use in compositions, applications and methods according to this disclosure.

"Aqueous-alcohol soluble proteins" and "aqueous-alcohol soluble protein compositions" are used interchangeably and mean the same thing. As is understand by persons of skill in the art, a protein may not be completely pure and may therefore be a protein composition including residual components due to its method of manufacture. For example, the protein may be a protein composition comprising a residual amount of alcohol as a result of the protein being extracted from a source using alcohol.

The phrase "no alcohol, waterborne dispersions" refers to waterborne dispersions of aqueous-alcohol soluble proteins, such as prolamins and for example zein, which are produced by dispersing a solid portion comprising the aqueous-alcohol soluble protein in a liquid portion without need for alcohol in the liquid portion. For the sake of clarity, no alcohol, waterborne dispersions include dispersions that are made using aqueous-alcohol soluble protein compositions that may include residual alcohol, for example because the protein compositions are extracted from a source using alcohol. In some embodiments, the no-alcohol, waterborne dispersions are substantially free of alcohol. In some embodiments, the no-alcohol, waterborne dispersions are alcohol-free. In some embodiments, the no-alcohol, waterborne dispersions may include alcohol (for example, the dispersions may include more than the residual amount of alcohol associated with the aqueous-alcohol soluble protein compositions, or the dispersions may not be substantially-free of alcohol), however the additional alcohol is not required in order for the dispersion to form. Similarly, this disclosure encompasses applications which may use the no-alcohol waterborne dispersions, such as end-products made using the no-alcohol, waterborne dispersions, even if those applications themselves use or include alcohol.

The phrases "without the benefit of alcohol" and "without the addition of alcohol" when referring to methods of making the no alcohol dispersions refer to alcohol that is in addition to any residual alcohol that may be associated with a component of the dispersion. For example, as a person of skill appreciates, and as previously discussed, some aqueous-alcohol soluble proteins from which dispersions according to this disclosure are made may have some associated alcohol due to being sourced using an alcohol extraction process. Accordingly, for example, when the specification refers to "a process which includes combining together an amount of water, an amount of an acid, an amount of an aqueous-alcohol soluble protein, and optionally an amount of an ester of a carboxylic acid to form a dispersion without the need for also adding an amount of an alcohol," the phrase does not exclude the possibility that some alcohol may be associated with a given component (such as the protein) as an artifact of its process of manufacture; however, no additional alcohol needs to be added when combining ingredients in order for the dispersion to form.

II. Dispersions

In some embodiments, compositions according to this disclosure comprise a solid portion and a liquid portion. The solid portion comprises an aqueous-alcohol soluble protein, whereas the liquid portion comprises water and an acid. The solid portion, despite comprising an aqueous-alcohol soluble protein, is dispersible in the liquid portion without the addition of alcohol in the liquid portion. In some embodiments, the solid portion may include an amount of alcohol due to the process by which the protein component is obtained (for example, alcohol extraction); however, no additional alcohol is required in order to form the waterborne dispersions consistent with this disclosure. The compositions may also optionally comprise an ester of a carboxylic acid. In some embodiments, the compositions are flowable, waterborne dispersions of aqueous-alcohol soluble proteins. In some embodiments, the compositions are the corresponding dried (for example freeze-dried) form of the no alcohol, waterborne dispersions.

In some embodiments, the aqueous-alcohol soluble protein is a protein derived from corn or grain, for example the aqueous-alcohol soluble protein may be extracted from a fermentation product of a corn- or grain-to-ethanol process. In some embodiments, the aqueous-alcohol soluble protein is derived from corn, wheat, milk, soy protein isolate, barley, rye, sorghum, or oats. In further embodiments, the aqueous-alcohol soluble protein is a prolamin, such as a prolamin derived from corn, wheat, barley, rye, sorghum, or oats. In other embodiments, the aqueous-alcohol soluble protein is chosen from zein, gliadin, glutenin, hordein, secalin, avenin, gluten, kafirin, whey, casein, soy protein, and combinations thereof.

In some embodiments, the aqueous-alcohol soluble protein is zein. As is known to persons skilled in the art, zein exists in several forms, including α-zein, β-zein, γ-zein, and δ-zein. See, for example, Lawton et al., "Chapter 9—Proteins of the Kernel," *J. Corn: Chemistry and Technology*; ($2^{nd}$ edition; pp. 313-354), and Esen, Asim, "A Proposed Nomenclature for Alcohol-Soluble Proteins (Zeins) of Maize (*Zea mays* L.)," *Journal of Cereal Science*, 5 (1987): 117-118, which are herein incorporated by reference in their entirety. Sources of zein, which may be used in embodiments according to this disclosure, may include one or more forms of zein. Examples of zein compositions suitable for use in embodiments according to this disclosure are provided in U.S. patent application Ser. No. 12/965,255 ("Zein Composition and Methods of Production"), assigned to POET, which is herein incorporated by reference in its entirety.

In some embodiments, the aqueous-alcohol soluble protein is a zein composition comprising at least one of β-zeins or γ-zeins. In some embodiments, the aqueous-alcohol soluble protein is a zein composition comprising a β-zein. In some embodiments, the aqueous-alcohol soluble protein is a zein composition comprising a γ-zein. In some embodiments, the aqueous-alcohol soluble protein is a β-zein. In some embodiments, the aqueous-alcohol soluble protein is γ-zein. In some embodiments, the aqueous-alcohol soluble protein is a zein composition comprising at least β-zeins and γ-zeins.

In some embodiments, the aqueous-alcohol soluble protein is a zein composition comprising β-zeins and/or γ-zeins, wherein the total amount of β-zeins and/or γ-zeins versus α-zeins in the zein composition is at least sufficient to form a no-alcohol, waterborne dispersion. In some embodiments, the aqueous-alcohol soluble protein is a zein composition comprising a total amount of β-zeins and/or γ-zeins of at least about 12% by mass of the total zein in the composition. In some embodiments, the total amount of β-zeins and/or γ-zeins is at least about 15%, at least about 20%, at least about 25%, at least about 30%, at least about 35%, at least about 40%, at least about 45% by mass of the total zein in the composition. In some embodiments, the total amount of β-zeins and/or γ-zeins ranges from about 12% to about 60% by mass of the total zein in the composition. In some embodiments, the total amount of β-zeins and/or γ-zeins ranges from about 12% to about 25% by mass of the total zein in the composition. In some embodiments, the total amount of β-zeins and/or γ-zeins ranges from about 12% to about 25% by mass of the total zein in the composition, or ranges from about 12% to about 20% by mass of the total zein in the composition, or ranges from about 12% to about 17% by mass of the total zein in the composition.

In some embodiments, the aqueous-alcohol soluble protein is a zein composition extracted from a fermentation product resulting from a dry-milling process, for example dried distillers grains ("DDG") or dried distillers grains with solubles ("DDGS") produced in a corn dry-milling process. In some embodiments, the zein composition is extracted from a fermentation product of a corn ethanol process according to U.S. patent application Ser. No. 12/651,401 ("the '401 application"), which is herein incorporated by reference in its entirety. In some embodiments, the aqueous-alcohol soluble protein is a zein composition according to U.S. patent application Ser. No. 12/965,255 ("the '255 application"), which is herein incorporated by reference in its entirety. The zein composition according to the '255 application is a by-product of a corn ethanol process. More specifically, the zein composition according to the '255 application is derived from a fermentation product of a corn ethanol process.

In some embodiments, the aqueous-alcohol soluble protein is a commercially-available zein composition such as INVIZ™ V740, available from POET, and which is extracted from dry mill ethanol process. The INVIZ™ V740 zein composition has the product specifications shown in Table 1 below.

TABLE 1

| | INVIZ ™ V740 Zein Product Specifications | | | | | | |
|---|---|---|---|---|---|---|---|
| Description | Dry Matter (%) | Moisture (%) | Crude Fat (% db) | Crude Protein (% db) | Ash (% db) | Percent α-zeins (%) | Percent β-zeins & γ-zeins (%) |
| INVIZ ™ V740 Zein | >92 | <8 | <3 | >87 | <4 | 83-88 | 12-17 |

Other zein compositions can be used, including compositions with similar specifications but for example a greater total amount of beta- and gamma-zeins (such as for example 20%, 25%, 30%, 35%, 40%, 45%, 50%, 55%, or 60% by mass of total zein), as well as other zein compositions such as described herein.

As suggested, the aqueous-alcohol soluble protein is not limited to zein but may include other proteins, such as other prolamins. For example prolamins derived from wheat gluten (i.e. a mixture of gliadin and glutenin) are also suitable for use in the dispersion compositions according to this disclosure. In addition, it is expected that other prolamins, for example prolamins derived from barley (Hordenin), prolamins derived from rye (Secalins), prolamins derived from oats (Avenin), and prolamins derived from sorghum (Kafirin) are also suitable for use in the dispersion compositions according to this disclosure. It is also expected that those prolamins or other aqueous-alcohol soluble proteins with characteristics similar to β-zeins and/or γ-zeins as opposed to α-zeins may also be suitable for use as the aqueous-alcohol soluble protein in accordance with this disclosure.

The dispersion compositions according to this disclosure also include a liquid portion, which comprises water and an acid. In some embodiments, the water is distilled water. In some embodiments, the acid may be inorganic acids or organic acids or combinations thereof. In some embodiments, the acids, for example the organic acids such as carboxylic acids, exhibit at least partial solubility in water. In some embodiments, the acids are soluble in water at room temperature. In some embodiments the acids are more soluble in water than decanoic acid, and oleic acid. In some embodiments, the acids are more soluble in water than sebacic acid, decanoic acid, and oleic acid. In some embodiments, the acids are more soluble in water than sebacic acid, decanoic acid, oleic acid, and oxalic acid. In some embodiments, the acid may have limited solubility in water, for example the acids may be more soluble in water than sebacic acid, decanoic acid, oleic acid and oxalic acid (such as succinic acid, which has a solubility of about 58 g/L or 5.8% (w/v) at 20 degrees C.) but a dispersion may still be formed, for example by adding heat to the acid before the ester and zein are added.

In some embodiments, the inorganic acid is hydrochloric acid.

In some embodiments, the organic acids include carboxylic acids, for example, monocarboxylic or polycarboxylic acids. In some embodiments, the carboxylic acids include those having the formula R—(COOH)n, where n ranges from 1 to 3, and where R is an n-functional organic radical. In some embodiments, the carboxylic acids may be: monocarboxylic acids chosen from formic acid, acetic acid, and propionic acid; dicarboxylic acids chosen from succinic acid, glutaric acid, adipic acid, and malic acid; tricarboxylic acids chosen from citric acid and trans-acontic acid; alpha-hydroxy carboxylic acids chosen from glycolic acid and lactic acid; keto-carboxylic acids chosen from glycolic acid, levulinic acid and ascorbic acid; sugar carboxylic acids chosen from D-gluconic acid; tartaric acid; and, combinations thereof.

In some embodiments, the compositions also include an ester of a carboxylic acid, which need not be a counterpart of the acid used in the liquid portion. In other words, in some embodiments, the acid may be mixed with one of its corresponding esters, such as citric acid may be mixed with trimethyl citrate, triethyl citrate, or tri-n-butyl citrate. However, in other embodiments, the acid need not be mixed with one of its corresponding esters, such citric acid may also be mixed the ethyl ester of lactic acid (ethyl lactate). In some embodiments, the esters of a carboxylic acid may be methyl esters of carboxylic acids, ethyl esters of carboxylic acids, propyl esters of carboxylic acids and/or butyl esters of carboxylic acids. In some embodiments, esters of carboxylic acids are chosen from: trimethyl citrate, dimethyl succinate, triethyl citrate, ethyl lactate, diethyl tartrate, tri-n-butyl citrate, dibutyl succinate, dibutyl sebacate, dibutyl tartrate, and combinations thereof.

In some embodiments, the compositions include an amount of aqueous-alcohol soluble protein, an amount of water, an amount of acid, and optionally an amount of an ester of a carboxylic acid. In some embodiments, the specific component (e.g. the specific protein, the specific acid, etc.) and relative amounts of each component are chosen to result in a dispersion of the protein in the water with a desired flowability and/or in which the protein remains dispersed for a desired period of time. In some embodiments, the specific component and relative amount of each component is chosen to maximize the amount of protein in the dispersion, while still achieving a desired flowability and desired time period for the dispersion to remain suspended. In some embodiments, the desired time period for the dispersion to remain suspended is overnight. In some embodiments, the desired time period for the dispersion to remain suspended may be less than about one minute. In some embodiments, the desired time period for the dispersion to remain suspended is at least about one minute (or for substantially one minute), at least about 1 hour (or for substantially an hour), at least about 2 hours (or for substantially 2 hours), at least about 3 hours (or for substantially 3 hours), at least about 4 hours (or for substantially 4 hours), at least about 5 hours (or for substantially 5 hours), at least about 6 hours (or for substantially 6 hours), at least about 7 hours (or for substantially 7 hours), or at least about 8 hours (or for substantially 8 hours). In some embodiments, a dispersion is considered to have remained suspended if it does not agglomerate or form a glob when stirred, heated and cooled.

In some embodiments, the amount of protein is chosen to achieve a desired solids content and/or achieve desired performance characteristics (such as for example stiffness, burst, and/or wet tensile strength in the case of a synthetic paper binder), where in some embodiments increasing the amount of protein may lead to the protein settling out of the dispersion, and decreasing the amount of protein may lead to a lower solids content and/or a less viscous dispersion.

In some embodiments, the amount of protein, and in some embodiments, the amount of zein, is at least about 0.2%, at least about 1%, at least about 5%, at least about 10%, at least about 15%, at least about 20%, at least about 25%, at least about 30%, at least about 35% by mass of the composition. In some embodiments, the amount of protein, and in some embodiments the amount of zein, ranges from about 0.2% to about 34.6% by mass of the composition, or ranges from about 0.2% to about 21.3% by mass of the composition.

In some embodiments, the amount of acid and/or ester of carboxylic acid are chosen to result in the protein being dispersed in the liquid phase. Without wishing to be bound by theory, it is believed that the acid and/or ester may function as a dispersant, for example by increasing the density of the continuous phase of the dispersion, increasing the viscosity of the continuous phase of the dispersion, and/or may shield protein particles from colliding with one another and agglomerating. Again without wishing to be bound by theory, it is believed that adjusting the pH by use of the acid may stabilize the emulsion by electrostatic repulsion. Accordingly, increasing the amount of acid and/or ester may result in a higher solids dispersion, a lower pH dispersion, a more stable dispersion, a higher density dispersion, and/or a higher (or lower) viscosity dispersion. And, decreasing the amount of acid and/or ester may result in a lower solids dispersion, a higher pH dispersion, a less stable dispersion, a lower density dispersion and/or a lower (or higher) viscosity dispersion.

In some embodiments, the amount of acid is at least 0.5%, at least about 1%, at least about 5%, at least about 10%, at least about 15%, at least about 20%, at least about 25%, at least about 30%, at least about 35%, at least about 40%, or at least about 45% by mass of the composition. In some embodiments, the amount of acid in the composition ranges from about 0.4% to about 48.1% by mass of the composition. In some embodiments, the amount of acid in the composition ranges from about 16.3% to about 48.1% by mass of the composition.

In some embodiments, the amount of ester is at least about 0.5%, at least about 1.0%, at least about 1.5%, at least about 2.0%, at least about 2.5%, at least about 3.0%, or at least about 3.5% by mass of the composition. In some embodiments, the amount of ester ranges from about 0.3% to about 53.1% by mass of the composition.

In some embodiments, the amount of water is chosen to achieve a desired flowability, where increasing the amount of water may lead to a lower solids dispersion, and/or a less viscous dispersion and decreasing the amount of water may lead to a higher solids dispersion, and/or a more viscous dispersion.

In some embodiments, the amount of water is at least about 30%, at least about 35%, at least about 40%, at least about 45%, at least about 50%, at least about 55%, at least about 60%, at least about 65%, at least about 70%, or at least about 75% by mass of the composition. In some embodiments, the amount of water ranges from about 38.1% to about 99.6% by mass of the composition.

In some embodiments, the dispersions are substantially free of, or are free of, one or more of: organic solvents, traditionally used primary or secondary zein solvents (except for acids in accordance with this disclosure) and additives as further described herein. A list of "traditional primary or secondary zein solvents" can be found in John W. Lawton, "Zein: A History of Processing and Use," Cereal Chemistry, vol. 79, No. 1, 2002, 1-18, which is herein incorporated by reference in its entirety. In some embodiments, the solvents (organic and primary and secondary traditionally used zein solvents) are one or more of: acetone and glycols such as diethylene glycol, propylene glycol and hexylene glycol. The referenced additives may be sodium hydroxide, rosin soap, alkali metal, ammonia, sulfonated oils, amine soaps, ammonia soaps of fatty acids, alkali soaps of fatty acids, rosin amines.

III. Methods

The disclosure also provides methods of making waterborne dispersions comprising an aqueous-alcohol soluble protein without the benefit of alcohol (e.g. without the need to add alcohol to the liquid to cause a dispersion to form). FIG. 1 is a flow diagram of an embodiment of a method of making a waterborne protein dispersion and the corresponding dried form of the dispersion. In general, as shown, in some embodiments, the methods comprise combining a set of components (which can occur in one or more steps) to form a dispersion without the addition of alcohol, wherein the set of components comprises an amount of aqueous-alcohol soluble protein, an amount of water, an amount of an acid, and optionally an amount of an ester of a carboxylic acid. In some embodiments, combining comprises stirring (which again can occur as one or more stirring steps). In some embodiments, combining comprises heating (also as one or more heating) steps. In some embodiments, combining comprises one or more stirring steps and one or more heating steps, wherein the heating and stirring may occur, for example, substantially simultaneously, substantially sequentially, or combinations thereof. For example, in some embodiments, stirring the combined components is sufficient to obtain a dispersion of the protein in water. For example, in some embodiments, wherein the combined components are at or below room temperature, the process includes stirring the components to achieve and/or maintain a dispersion of the protein in water.

The nature and amount of each component (e.g. protein, water, acid, ester) that is combined to form a dispersion according to the methods of this disclosure may be as described above in Section II ("Dispersions") of this disclosure. In some embodiments, as provided in the same Section II ("Dispersions") of this disclosure, the aqueous-alcohol soluble protein is a prolamin, for example zein. In some embodiments, the protein or prolamin or zein, which is combined with water and other components to form a dispersion is in the form of a finely ground powder. In some embodiments, the protein or prolamin or zein is in the form of flakes. In some embodiments, all of the components are nontoxic. In some embodiments, all of the components are food grade materials. In some embodiments, all of the components are pharmaceutically-acceptable.

As shown in FIG. 1, the method may optionally further comprise drying the waterborne dispersion to obtain a dried, waterborne protein composition.

In some embodiments, the waterborne dispersion may settle with time, for example they may settle almost immediately after stirring is stopped, or the protein may remain dispersed in the liquid for a longer period of time after stirring is stopped. In some embodiments, the protein may remain dispersed in the liquid for at least about one minute (substantially about one minute) or less. In some embodiments, the protein may remain dispersed in the liquid for at least about one hour (substantially one hour), at least about two hours (substantially two hours), at least about three hours (substantially three hours), at least about four hours (substantially four hours), at least about five hours (substantially five hours), at least about six hours (substantially six hours), at least about seven hours (substantially seven hours), at least about eight hours (substantially eight hours), or at least overnight (substantially overnight). In some embodiments, the methods involve re-dispersing the protein in the liquid after the protein has settled, for example by stirring.

In some embodiments, the methods further comprise diluting the dispersions with additional water. Without wishing to be bound by theory, it is believed that charge may repel the suspended particles and that if the charge is adjusted, for example by adjusting the pH, the particles may not be sufficiently repelled and may be attracted to each other, begin to agglomerate, and cause the dispersion to settle out. In such a case, if the addition of water raises the pH, the dispersion may begin to agglomerate and settle out. Nevertheless, in some embodiments, the solid remains dispersed despite the addition of water, for example as long as the pH of the subsequent dispersion is not significantly raised.

More specifically, in some embodiments (and as exemplified in Examples 2, 3 and 5) combining comprises: dissolving the acid in the water to form a first composition; and, mixing the ester (if present) and the protein into the first composition to form a second composition. In some embodiments, combining further comprises heating and stirring the second composition, for example until the second composition begins to reflux, followed by cooling and stirring the second composition to about room temperature. As a person of skill understands, heating and/or stirring may also be used to assist in preparing the first composition.

More specifically, in other embodiments (and as exemplified in Example 6), combining comprises: dissolving the ester and a portion of the acid in a portion of the water to form a first liquid component; dissolving the remaining portion of acid in a second portion of water to form a second liquid component; adding together the first liquid component and the protein to form a first mixture; stirring and heating the first mixture; heating the second liquid component; heating the remaining portion of water; while stirring, alternatively adding the heated second liquid component and the heated water in one or more steps to the first mixture to form a final mixture of desired viscosity; and, cooling while stirring the final mixture to room temperature.

In some embodiments (and as exemplified in Example 7), the method further comprises drying the dispersion to form a re-dispersible solid form of the composition. In some embodiments, drying the composition comprises freeze-drying the composition. In further embodiments, the method further comprises re-dispersing the dried composition in water. In some embodiments, the dispersion is dried as a means to assist long-term storage or transportation of the compositions.

IV. Applications

The present disclosure also provides for methods of using dispersions according to this disclosure in product applications, as well as methods of making the product applications. In some embodiments, the dispersions can be applied "as is"—for example, upon combining the aqueous-alcohol soluble protein, water, and acid (and optionally an ester of a carboxylic acid and/or other desired components) to form a dispersion. In some embodiments, additional components may be added to the dispersions (including alcohol) before incorporation into an end-use application. In some embodiments, the dispersions are dried and/or re-dispersed before incorporation into an end-use application. Examples of end-use applications into which the (wet and/or dried, as applicable) dispersions may be incorporated include: adhesives, paper binders, paper coatings, paints, varnishes, etc. Examples of the use of a dispersion according to this disclosure as paper binder are provided in Examples 8-10. An example of the use of a dispersion according to this disclosure in a paint composition is provided by Example 11.

V. Examples

The methodologies used for measuring properties in the Examples herein of product applications made using dispersions according to the disclosure are provided in Table 1, below. Properties of commercial products are as reported from specification sheets.

Samples were prepared for study. First, the mass of each sample to combine with 1 mL of solvent was calculated such that each solution would be 2% (w/v) crude protein. Next, the calculated amount of sample was weighed out and 1 mL 70% (w/w) aq ethanol, 5% (v/w) 2-mercaptoethanol, 0.5% (w/w) sodium acetate solvent solution was pipetted into each micro-centrifuge tube. A thin piece of wire and a vortex mixer were used to break up any aggregated sample globs in the solution. The micro-centrifuge tubes were placed in a hot water bath set to 70 degrees C. for 1 hour. Then aggregates were broken up as before and the samples were centrifuged at 12000 RCF for 5 minutes. The supernatant was decanted into a vial. The sample was then diluted to 10× by pipetting 0.250 mL of supernatant and mixing with 2.250 mL of 55% (v/v) aq iso-propanol, 5% (v/v) 2-mercaptoethanol. Finally, the dilution was filtered with a PVDF 0.2 μm syringe filter into HPLC vials.

The samples were then analyzed using a Reverse Phase-High Performance Liquid Chromatography ("RP-HPLC") technique. One such RP-HPLC procedure that can be used to determine percent α-zeins vs. percent combined β-zeins and γ-zeins consistent with this disclosure is outlined in *Cereal Chem: "Sorghum* Protein Extraction by Sonication and its Relationship to Ethanol Fermentation," 85(6): 837-842

TABLE 1

Methods of Measuring Product Properties

Standard Method Used

| | |
|---|---|
| Paper Binder Test | |
| Stiffness | TAPPI T 543 "Bending resistance of paper (Gurley-type tester)" |
| Opacity | TAPPI T 425-om-01 (2007) "Opacity of paper (15/d geometry, illuminant A/2°, 89% reflectance backing and paper backing" |
| Tear | TAPPI T 414 "Internal Tearing Resistance of Paper" |
| Burst | TAPPI T 403 "Bursting Strength of Paper." |
| Dry Tensile | TAPPI T 404 "Tensile breaking strength and elongation of paper and paperboard (using pendulum-type tester)" |
| Wet Tensile | TAPPI T 456 om-03 "Tensile breaking strength of water-saturated paper and paperboard ("wet tensile strength")" |
| Abrasion | TAPPI T 476 om-06 "Abrasion loss of paper and paperboard (Taber-type method)" |
| Porosity | Standard Coresta method 40 - Coresta Machine |
| Pore Size | WSI Porometer Micro ASTM F316-03[2011] |
| Hercules Size Test | TAPPI T 530 om-02 "Size test for paper by ink resistance (Hercules-type method)" |
| OGR | TAPPI T 559 pm-96 Grease Resistance test for paper and paperboard |
| Fold Endurance | TAPPI T 511 "Folding endurance of paper (MIT tester)" |
| Paper Coating Test | |
| Opacity | TAPPI T 425-om-01 (2007) "Opacity of paper (15/d geometry, illuminant A/2°, 89% reflectance backing and paper backing" |
| Brightness | TAPPI T 525-om-06 (2007) "Diffuse brightness of paper, paperboard and pulp (d/0) - ultraviolet level C" |
| Gloss at 60° | ASTM D523 ASTM D2457 ASTM C2426 - BYK Mallinckrodt Gloss Meter |
| Gloss at 20° | TAPPI T 653 om-07 "Specular gloss of paper and paperboard at 20 degrees" |
| Paint Test | |
| Thickness | TAPPI T 411 om-89 (Total thickness of film) |
| Density | GSM divided by Thickness (microns) |
| Flexibility | TAPPI T 543 om-94- Bending Resistance: Gurley Stiffness |
| Hardness-D | ASTM D2240 - 05(2010) Standard Test Method for Rubber Property-Durometer Hardness |
| Thickness | TAPPI T 411 om-89 (Total thickness minus thickness of substrate backing) |
| Opacity | TAPPI T 425 om-91 (opacity of clear substrate plus painted coating) |
| Scratch Resistance | ASTM D5178 - 98(2008) Standard Test Method for Mar Resistance of Organic Coatings (Scratch) |
| Cohesion | ASTM D5178 Garnder Scrape Adhesion Hoffman Type Stylus |
| Scrape Resistance | ASTM D2197 - 10 Standard Test Method for Adhesion of Organic Coatings by Scrape Adhesion |
| Gloss | ASTM D523 - 08 Standard Test Method for Specular Gloss |
| Brightness | TAPPI T 452 om-92 Carl Zeiss Brightness Elrephro |

1. Method of Measuring Percent α-Zeins v Combined β-Zeins and γ-Zeins.

(2008), which is herein incorporated by reference in its entirety. More specifically, the RP-HPLC procedure is described in the Materials and Methods Protein Characterization section of the article on the bottom of page 838.

Another appropriate method for characterizing distribution in a sample in accordance with this disclosure is provided in "Zein Composition in Hard and Soft Endosperm of Maize," M. A. Dombrink-Kurtzman and J. A. Bietz, *Cereal Chem:* 70(1): 105-108, which is also herein incorporated by reference in its entirety.

In the present example, RP-HPLC of reduced proteins was conducted using an Agilent 1100 HPLC system equipped with a Juptior C18 2.0×150 mm column (Phenomenex) with guard columns of the same materials. Samples (10 µL each) were injected and separated with a continuous linear gradient of 0.1% tri-fluoracetic acid (TFA) (solvent A) and acetonitrile containing 0.1% TFA (solvent B), in which solvent B increased from 28 to 60.5% over 50 min and then was held 10 min (Bean et al 2000). Flow rate was 0.5 mL/min with column temperature maintained at 50 degrees C. Proteins were detected by measuring UV absorbance at 214 nm. Peak areas were expressed in arbitrary units based on millivolts of detector output.

Figure 2:
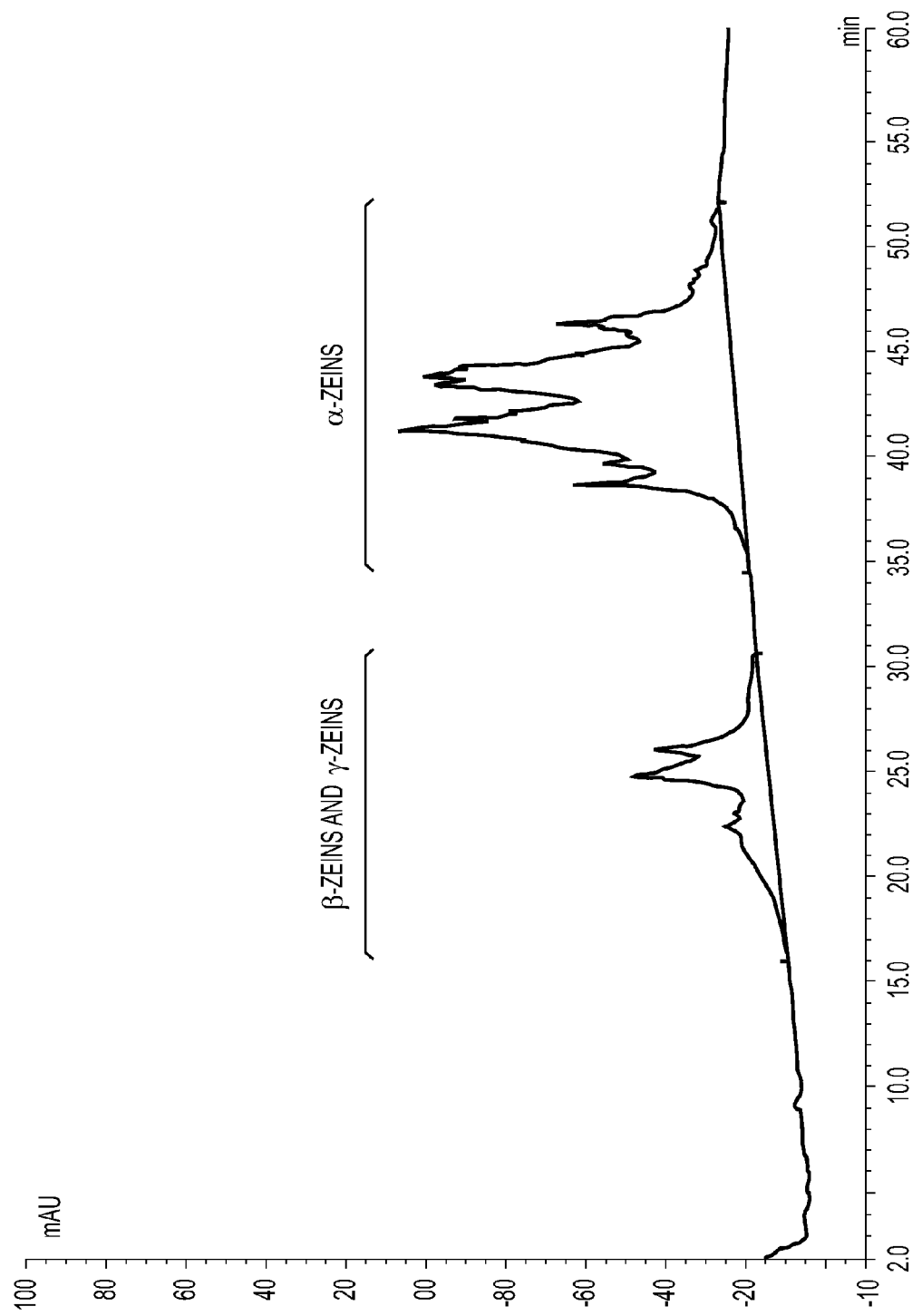
FIG. 2 is a chromatogram showing the combined amount of beta-zeins and gamma-zeins in a zein composition suitable for use in compositions in accordance with some embodiments of this disclosure.

The retention time for β-zeins and γ-zeins overlap using this technique and thus the percent relative peak areas reported are a total sum of the β-zeins and γ-zeins relative peak areas vs. the total sum of α-zeins percent relative peak areas. FIG. 2 is a representative chromatogram of zein distribution in a sample, which was produced by the described procedure.

2. Method of Preparation of Waterborne Zein Compositions

Distilled water and acid are added to a flask or similar container and allowed to dissolve. With vigorous agitation, the ester of the carboxylic acid and finely ground zein are added to the unheated liquid in the container. The combined components are continuously stirred and allowed to heat. When the liquid begins to reflux (approximately 98 degrees C.), it is removed from the heat and allowed to cool to room temperature, while continuing to stir. The color of the dispersions generally lightens during heating. The waterborne prolamin is ready for application.

Table 2 provides examples of suitable components and suitable ranges for the amount of each component in the zein dispersions, which can be produced according to the described procedure. In the embodiments encompassed by Table 2, the first set of ranges was determined based on what would stay suspended and not agglomerate and form a glob when stirred, heated, and cooled. The second set of ranges was determined based on stability (which for the purposes of the present embodiment was defined as staying suspended when allowed to settle overnight) and no other performance characteristic.

TABLE 2

Examples of Approximate Water/Citric Acid/Triethyl Citrate/INVIZ ™ Dispersion Ranges

| Component | Approximate Typical Ranges | | Approximate Preferred Ranges | |
|---|---|---|---|---|
| | Minimum (Mass %) | Maximum (Mass %) | Minimum (Mass %) | Maximum (Mass %) |
| Water | <38.1% | >99.6% | <38.1% | >99.6% |
| Acid | 0.4% | >48.1% | 16.3% | >48.1% |
| Ester of Carboxylic Acid | 0.0% | 53.1% | 0.3% | 53.1% |
| Protein | 0.2% | >34.6% | 2.2% | 21.3% |
| Calculated Percent Solids | <0.4% | 50% | <0.4% | 65.9% |

| Description | Approximate Typical Ranges | | Approximate Preferred Ranges | |
|---|---|---|---|---|
| | Minimum | Maximum | Minimum | Maximum |
| pH | 0.7 | 5.7 | 0.7 | 3.0 |
| Heating Temperature | Room Temp | 100 | 60 | 100 |
| Zein Protein Percent α-Zeins | <56% | <100% | <56% | <84.6% |
| Zein Protein Percent β-Zeins & γ-Zeins | >0% | >44% | >15.4% | >44% |
| Zein Percent Protein (db) | <77.1% | >95.9% | 87.5% | >95.9% |

3. Preparation of Three Waterborne Zein Dispersions

Three waterborne zein dispersions were prepared according to the method of Example 2, according to the formulations provided in Table 3, below.

TABLE 3

Waterborne Zein Dispersion Composition Formulas

| Dispersion # | Component Description | | Component Mass (g) | Component Density (g/mL) | Component Volume (mL) | Component Mass Percent (%) | Calculated Percent Solids (%) |
|---|---|---|---|---|---|---|---|
| 1 | H2O | Distilled | 111.0 | | | 73.0% | 27.0% |
| | Citric Acid | ≥99.5% Purity | 17.5 | | | 11.5% | |
| | Triethyl Citrate | 99% Purity | 3.60 | 1.137 | 3.16 | 2.4% | |
| | Zein | INVIZ ™ V740 | 20.0 | | | 13.1% | |
| 2 | H2O | Distilled | 111.0 | | | 57.5% | 42.5% |
| | Citric Acid | ≥99.5% Purity | 35.0 | | | 18.1% | |
| | Triethyl Citrate | 99% Purity | 7.20 | 1.137 | 6.33 | 3.7% | |
| | Zein | INVIZ ™ V740 | 40.0 | | | 20.7% | |
| 3 | H2O | Distilled | 111.0 | | | 59.1% | 40.9% |
| | Citric Acid | ≥99.5% Purity | 30.6 | | | 16.3% | |
| | Triethyl Citrate | 99% Purity | 6.3 | 1.137 | 5.53 | 3.3% | |
| | Zein | INVIZ ™ V740 | 40.0 | | | 21.3% | |

4. Waterborne Zein Dispersion Characteristics

Certain characteristics of the dispersions of Example 3 are provided in Table 4 below. The characteristics of these three dispersions are compared to the characteristics of a zein emulsion prepared according to Example 13 of co-pending U.S. patent application Ser. No. 13/548,839 having the title "Water-Based Prolamin Compositions, Methods of Making Water-Based Prolamin Compositions, and Applications Thereof," filed on Jul. 14, 2011 and assigned to POET, and which is herein incorporated by reference in its entirety (hereinafter "Example 13 emulsion"). The characteristics of the three dispersions are also compared to two commercial products: styrene-butadiene rubber (SBR) (Dow 275NA) and commercial acrylic binder (Rhoplex B-15 15J).

TABLE 4

Waterborne Zein Dispersion Characteristics

| Description | Percent Solids (%) | pH |
|---|---|---|
| Dispersion #1 | 30.8% | 2.0 |
| Dispersion #2 | 44.3% | 2.1 |
| Dispersion #3 | 42.6% | 2.1 |
| Example 13 | 33.5% | 2.2 |
| SBR | 48% | 7.4 |
| Acrylic | 46% | 5.4 |

In addition, the mean particle size of dispersion No. 1 measured in water in using a Horiba LA-950 Particle Size Analyzer using a refractive index of 1.53 was 2.18 µm. The mean particle size of the Example 13 emulsion, measured in the same manner, was 36.63 µm. Volatile Organic Compounds ("VOCs") were tested according to EPA Method 24. Dispersion No. 3 had 0 g VOC per liter of coating. The emulsion of Example 13 was measured at 26 g VOC per liter of coating.

5. Preparation of Additional Waterborne Zein Dispersions

Additional waterborne zein dispersions were successfully made in accordance with the method of Example 2. For purposes of this example, the "success" of a dispersion was determined by the ability of the dispersion to stay suspended and not agglomerate or form a glob when stirred, heated and cooled. It should be noted that many successful dispersions were made in which the carboxylic acids and esters of carboxylic acids didn't correspond with one another (ex. citric acid can be mixed with one of its corresponding esters (trimethyl citrate, triethyl citrate, tri-n-butyl citrate), but can also be mixed with the ethyl ester of lactic acid (ethyl lactate)).

Figure 4A:
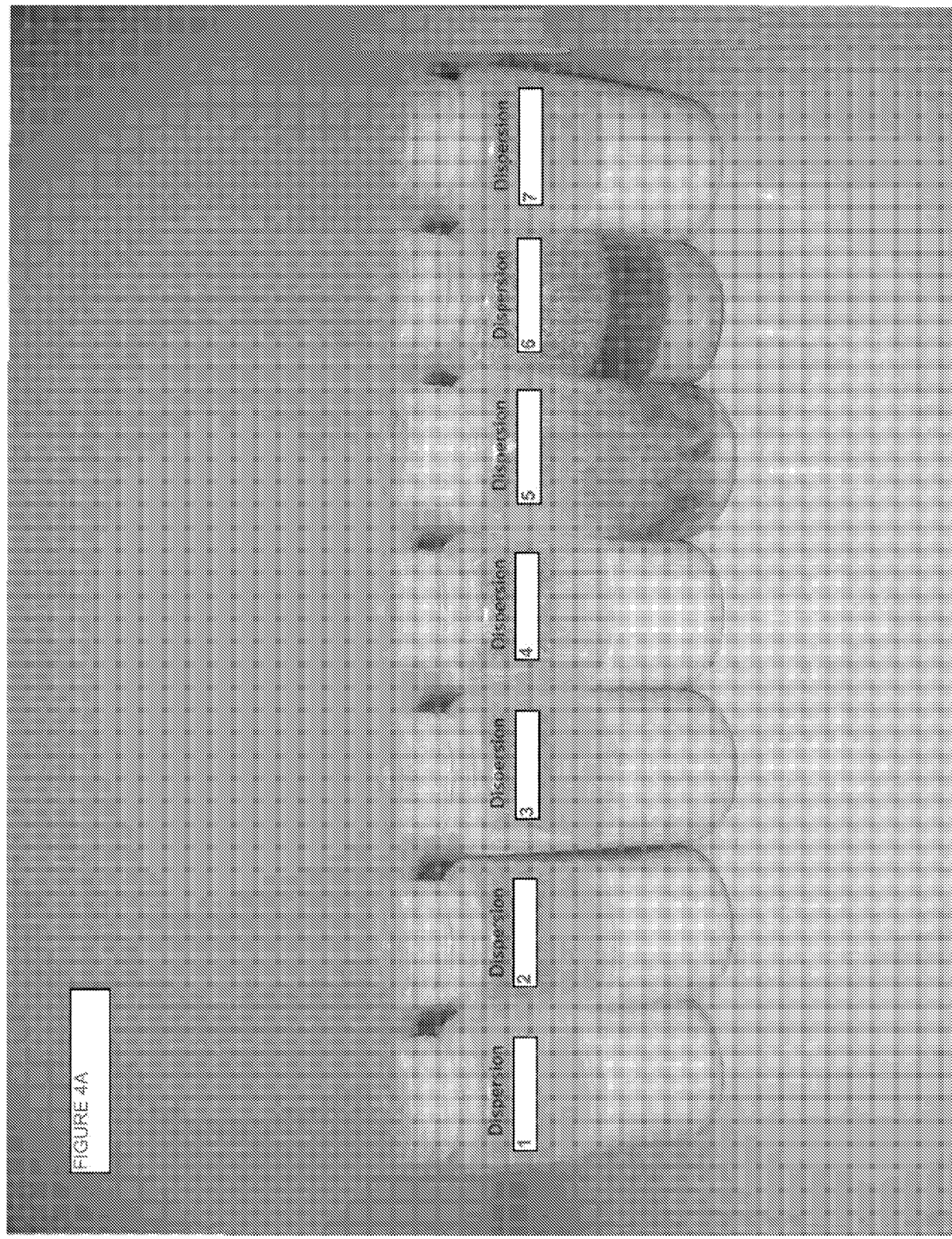
FIG. 4A is a black and white photograph of compositions comprising aqueous alcohol soluble protein.
Figure 4B:
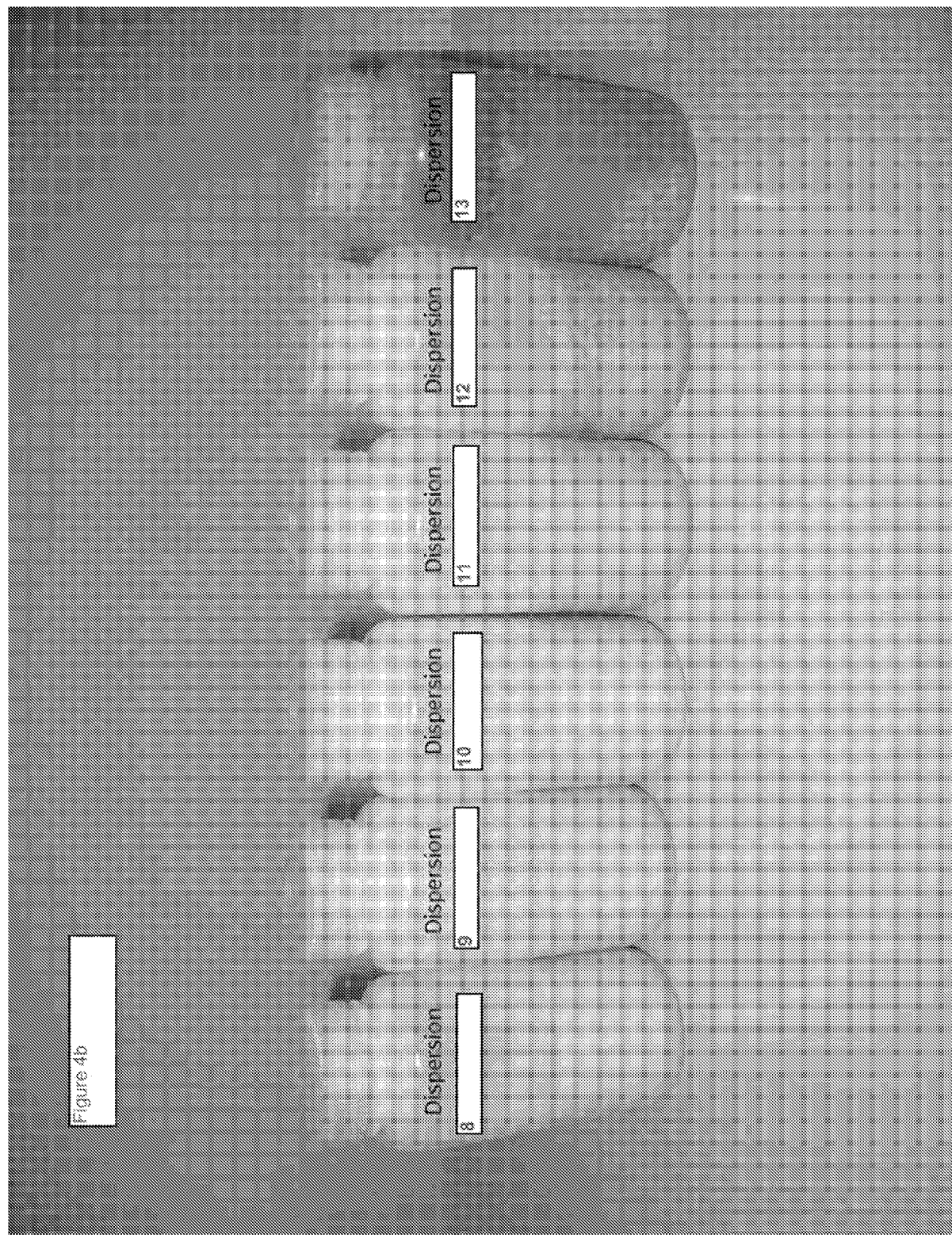
FIG. 4B is a black and white photograph of additional compositions comprising aqueous alcohol soluble protein.
Figure 4C:
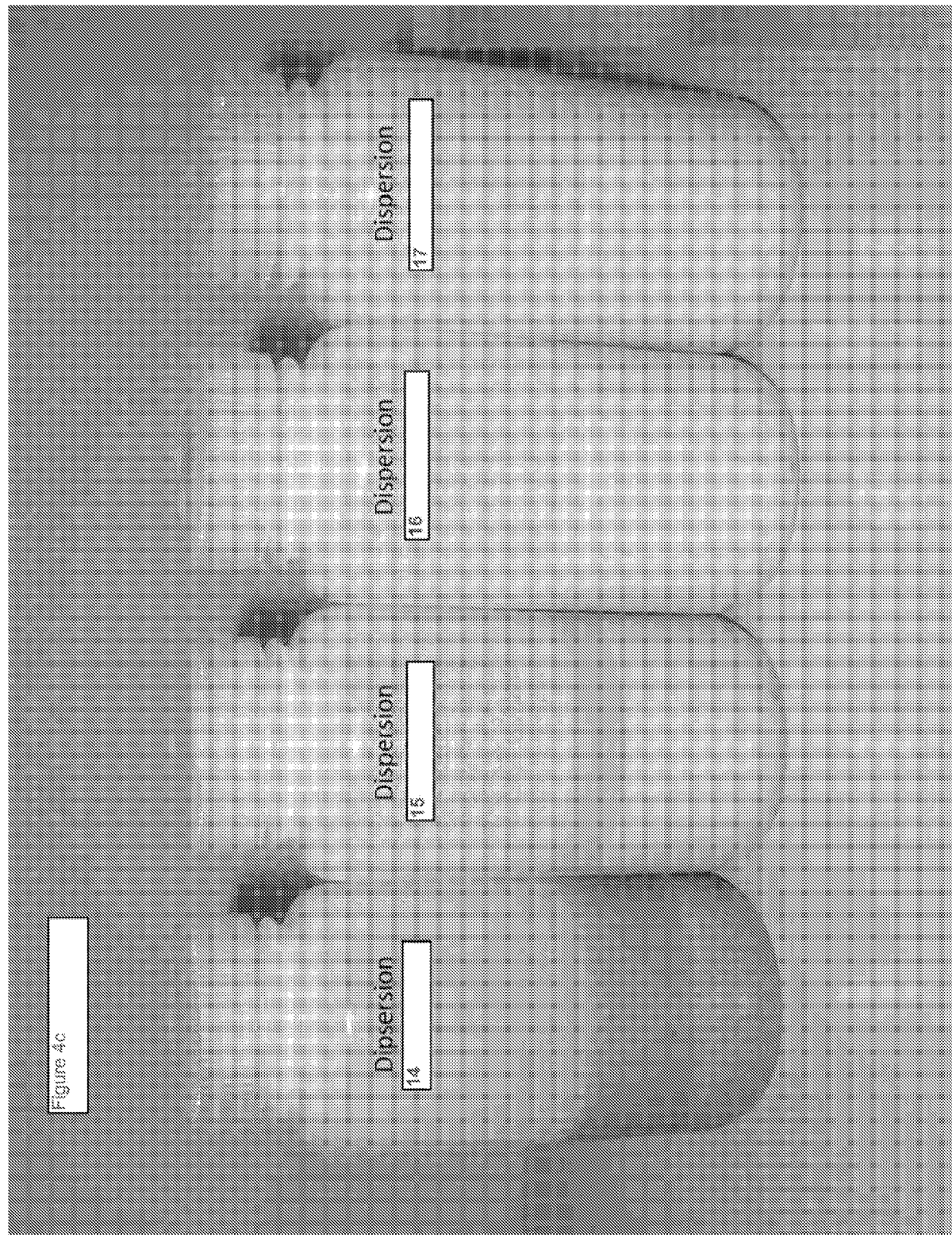
FIG. 4C is a black and white photograph of yet additional compositions comprising aqueous alcohol soluble protein.

Twenty-eight additional dispersions having the same formulation as Dispersion No. 1 in Example 3, were successfully made with the specific substitution of one of the acid, the ester, or the protein as follows. Citric acid was substituted by formic acid, acetic acid, propionic acid, succinic acid, glutaric acid, adipic acid, malic acid, citric acid, trans-aconitic acid, glycolic acid, lactic acid, levulinic acid, ascorbic acid, D-gluconic acid, tartaric acid, and hydrochloric acid. Tiethyl citrate was substituted by trimethyl citrate, dimethyl succinate, triethyl citrate, ethyl lactate, diethyl tartrate, tri-n-butyl citrate, dibutyl succinate, and dibutyl sebacate. INVIZ™ V740 was substituted by protein derived from wheat gluten (mixture of gliadin and glutenin), protein derived from milk (casein) and protein derived from soy protein isolate. Additional dispersions were also successfully made using different combinations of the above-mentioned carboxylic acids and esters of carboxylic acids. FIGS. 4A-4C (reference numbers 1-4, 6-11, 15-17) are black and white photos of some of the above successful dispersions. It is expected that additional dispersions may be successfully made by substituting INVIZ™ V740 with zeins of varying purities (protein contents) and varying percent α-zeins vs. combined percent β-zeins and γ-zeins.

Additional substitutions were also made, but the solid component formed a big glob as shown in FIGS. 4A-4C. Specifically, as shown in FIG. 4A, sebacic acid 5 was used as the acid, but did not completely dissolve in water at room temperature, and turned into a big glob with heat. As shown in FIG. 4B, decanoic acid 12 was substituted as the acid, also did not completely dissolve in water at room temperature, and turned into a big glob at about 30 degrees C. Also as shown in FIG. 4B, when oleic acid 13 was substituted as the acid, it mixed well with water and TEC until a certain amount of zein was added at which point it turned into a big glob. In another instance, a dispersion was formed but produced a stringy glob when heated. Specifically, as shown in FIG. 4C, oxalic acid 14 was substituted as the acid and didn't appear fully dissolved at room temperature but produced a whitish liquid. Although oxalic acid produced a normal looking dispersion when zein was added, it turned to a stringy glob with heat. Without wishing to be bound by theory, it is believed that these results (either forming a big glob or forming a dispersion then a stringy glob upon adding heat) for certain acids are due to the relatively poor solubility of the specific acids in water (for example, due to the fact that they would not fully dissolve in water at room temperature).

Finally, a big glob formed when the zein composition including beta-zeins and gamma-zeins was substituted for a zein composition containing only (about 100%) alpha-zeins.

6. Alternative Method of Preparation of Zein Dispersion

The waterborne prolamin dispersions were also prepared by an alternative method, which resulted in similar stability. The method involved dissolving 20.0 g citric acid and 5.3 mL of the triethyl citrate in 15.0 g distilled water. This saturated solution was added to 40.0 g ground INVIZ™ (zein) in a flask. With stirring, the flask temperature was set to 70° C. The slightly wet clumps became a brown colored taffy as the temperature increased. The temperature maxed out at ~85° C. 5 mL heated distilled water was slowly added to the flask and allowed to mix. In a separate container, the remaining citric acid (10.6 g) was added to 5 mL distilled water. This heated, saturated solution was added to the flask. After 5 minutes, 5 mL heated distilled water was slowly added to the flask and allowed to mix. Every 10 minutes for 30 minutes, 10 mL heated distilled water was slowly added to the flask. The brown colored taffy became a butterscotch colored pudding/paste. Every 5 minutes, 5 mL heated distilled water was added until all (111.0 g total) of the distilled water was added. The butterscotch colored pudding/paste became a butterscotch colored liquid. Depending on losses due to evaporation and the desired solids content and viscosity, additional (ex. 20 mL) heated distilled water may be added. The liquid was removed from heat and allowed to continue stirring until it cooled to room temperature. The waterborne prolamin dispersion was ready for application.

7. Method of Drying Waterborne Zein Dispersions and Redispersing in Water

Freeze waterborne prolamin dispersions, such as Dispersions Nos. 1-3 of Example 3, in a freeze dry flask. Freeze dry the dispersion. Finely grind the freeze dried dispersion. With vigorous agitation, slowly add the freeze dried dispersion to distilled water in the desired concentration. The re-dispersed dispersion may not have the same stability as the original dispersion of equal solids content and may tend to settle more quickly.

In alternative embodiments, other drying methods, such as appropriate dryers, are used to dry the waterborne prolamin dispersions. In further embodiments, the dried dispersions are redispersed at a later time.

In any of the above embodiments, the waterborne prolamin dispersions may be waterborne prolamin dispersions (or waterborne protein dispersions) consistent with this disclosure. In some embodiments, the waterborne prolamin dispersions may be substituted by other prolamin (or other protein) dispersions. For example, in some embodiments, the prolamin dispersions may be made by mixing the appropriate amounts of acid, ester of carboxylic acid with zein solubilized in aqueous alcohol according to POET's current zein manufacturing process before drying the solution using a double drum vacuum dryer to drive off the ethanol and water. In any case, the dried dispersion may then be re-dispersed at a later time.

Figure 3:
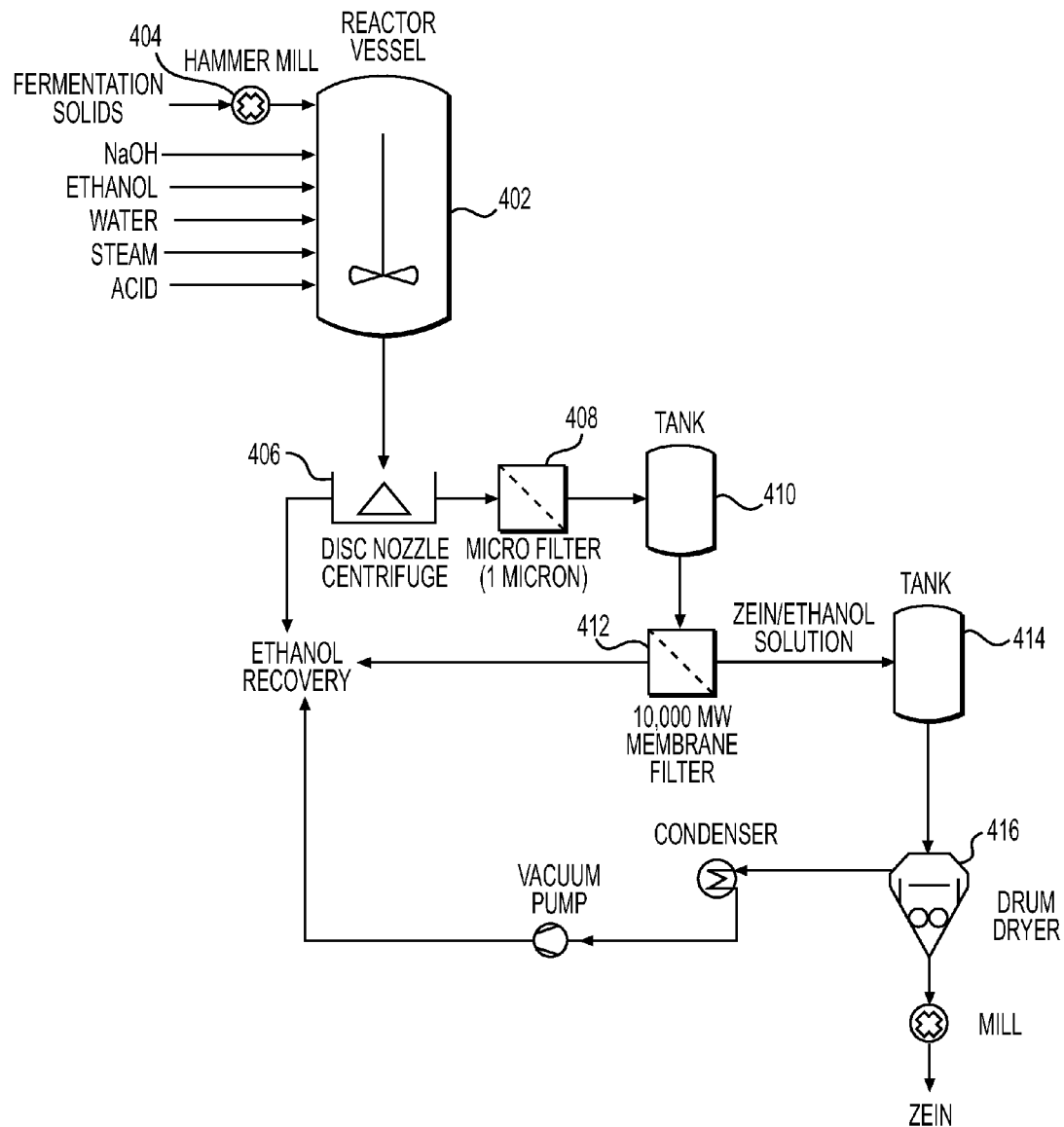
FIG. 3 is a schematic block diagram of equipment which may be used for a system of extracting zein from fermented solids.

FIG. 3 is a schematic block diagram of equipment which may be used for a system for extracting zein from fermented solids, which zein may be used in the present example. FIG. 3 corresponds to FIG. 4 of the '401 application referenced above. It is expected that the addition of the acid and ester of carboxylic acid to the purified zein retentate would most likely occur in the dryer feed tank (414). (This is equivalent to adding the acid and ester of carboxylic acid to the retentate in FIG. 5A, 5B, 6A, 6B of the same '401 patent application.) For some applications, appropriate amounts of acid, ester of carboxylic acid could be added to unpurified zein in aqueous ethanol which would most likely occur in the centrate tank (410) depicted in FIG. 3. This solution could then be dried using the double drum vacuum dryer. The dried dispersion could then be re-dispersed at a later time.

8. Preparation of Synthetic Paper Using Waterborne Zein Dispersion as Binder

Dispersions #1-3, Example 13 emulsion, and a commercial acrylic binder (Rhoplex B-15J) were added as binders at about 15% weight to 60 g/m² sheet of polyester synthetic fiber. Hand sheets (TAPPI method T205; 6 by 6 inch sheet) were prepared using a TAPPI Standard handsheet mold. These handsheets were then processed through a Euclid Size Press Coater which saturated them with binder. A further handsheet was similarly made except without the addition of binder. The samples were dried using a convection oven at 63° C. Various properties of the handsheets were measured. The results are presented in Table 5.

TABLE 5

Synthetic Base Sheet (PET) Test Results

|  | Final Binder Weight (g/m²) | % Binder (% w/w) | Thickness (microns) | Density (g/cm³) | Stiffness (gram-force) | Opacity (%) |
| --- | --- | --- | --- | --- | --- | --- |
| No Binder | 60 B | 0 B | 240 D | 0.25 AB | 63 D | 93 A |
| Acrylic | 70 A | 15 A | 264 C | 0.26 A | 96 C | 90 D |
| Emulsion 13 | 70 A | 15 A | 288 B | 0.24 BC | 164 B | 93 AB |
| Dispersion #1 | 70 A | 15 A | 306 A | 0.23 D | 183 AB | 92 BC |
| Dispersion #2 | 70 A | 15 A | 298 AB | 0.23 CD | 173 B | 92 C |
| Dispersion #3 | 70 A | 15 A | 296 AB | 0.24 CD | 200 A | 92 C |

|  | Tear MD (gram-force) | Tear CD (gram-force) | Burst (psig) | Tensile (Dry) Machine Direction (kg/15 mm) | Tensile (Dry) Cross Direction (kg/15 mm) | Tensile (Wet) Machine Direction (g/15 mm) |
| --- | --- | --- | --- | --- | --- | --- |
| No Binder | 61 B | 78 C | 6 D | 1.7 C | 0.8 D | 680 C |
| Acrylic | 150 A | 205 A | 52 A | 3.9 A | 1.8 BC | 1338 B |
| Emulsion 13 | 128 A | 140 B | 20 C | 3.1 B | 1.6 C | 1050 B |
| Dispersion #1 | 145 A | 193 A | 46 AB | 4.3 A | 2.2 A | 2038 A |
| Dispersion #2 | 140 A | 188 AB | 40 B | 3.8 A | 1.9 ABC | 1875 A |
| Dispersion #3 | 140 A | 183 AB | 42 B | 3.8 A | 2.1 AB | 1800 A |

|  | Tensile (Wet) Cross Direction (g/15 mm) | Abrasion (strokes) | Porosity (Coresta Units) | Minimum Pore Size (microns) | Maximum Pore Size (microns) | Mean Flow Pore Size (microns) |
| --- | --- | --- | --- | --- | --- | --- |
| No Binder | 455 D | 1 B | 1116 A | 5.4 B | 25.6 A | 8.7 B |
| Acrylic | 663 BC | 2 AB | 1013 B | 7.8 A | 16.0 A | 10.6 AB |
| Emulsion 13 | 481 CD | 1 B | 931 C | 7.8 A | 17.3 A | 10.7 AB |
| Dispersion #1 | 913 A | 1 B | 1071 AB | 8.3 A | 25.1 A | 12.9 A |
| Dispersion #2 | 869 A | 2 A | 1092 A | 7.8 A | 17.8 A | 11.2 AB |
| Dispersion #3 | 850 AB | 2 A | 1082 A | 8.1 A | 17.3 A | 11.2 AB |

|  | Hercules Size Test (seconds) | Fold Endurance (# of Fold Cycles) |
| --- | --- | --- |
| No Binder | 0 B | 25 B |
| Acrylic | 7 A | 2968 A |
| Emulsion 13 | 0 B | 30 B |
| Dispersion #1 | 0 B | 253 B |
| Dispersion #2 | 0 B | 124 B |
| Dispersion #3 | 0 B | 304 B |

Means within a column not sharing an uppercase letter are significantly different ($P < 0.05$).

The dispersions performed equally well to acrylic and the Example 13 emulsion. Without wishing to be bound by theory, it is believed that the dispersions performed best in wet tensile and burst because of their tackiness and flexibility. The dispersions and Example 13 emulsion exhibited increased stiffness relative to acrylic.

9. Preparation of Cellulosic Paper Using Waterborne Zein Dispersions as a Paper Binder Dispersions #1-3, the Example 13 emulsion, and a commercial acrylic binder (Rhoplex B-15J) were added as binders at about 15% weight to 50 g/m2 sheet of cellulosic paper. The handsheets were made from Hinton HIBRITE Northern Bleached Softwood Kraft (NBSK) pulped to ° 25 SR (Schopper Riegler) using a Voith valley beater and then made using a 10 inch by 12 inch Williams hand sheet mold. The samples were blotted and then dried using a convection oven at 63° C. These handsheets were then processed through a Euclid Size Press Coater which saturated them with binder. A further handsheet was made without the addition of binder. Various properties of the handsheets were measured. The results are presented in Table 6.

10. Preparation of Cellulosic Paper Using Waterborne ZeinDispersions as a Coating Dispersions #1-3, the Example 13 emulsion, and a high quality commercial styrene-butadiene rubber (SBR) (Dow 275NA) were used to coat hand sheets. The handsheets were made from Hinton HIBRITE Northern Bleached Softwood Kraft (NBSK) with 1% by weight HERCON alkyl ketene dimer (AKD) and 1% by weight Imerys kaolin clay pulped to ° 25 SR (Schopper Riegler) using a Voith valley beater and then made using a 10 inch by 12 inch Williams hand sheet mold. The samples were blotted and then dried using a convection oven at 63° C. After drying, the sheets were coated on one side using a straight through two roll metering (size press) Euclid coater. The coated sheets were calendered using a Wheeler Roll Co. supercalender at 500 PSI and ambient temperature. Various properties of the handsheets, including an uncoated handsheet, were measured. The results are presented in Table 7.

TABLE 6

Cellulosic (NBSK) Hand Sheet Paper Binder Test Results

|  | Final Binder Weight (g/m$^2$) | % Binder (% w/w) | Thickness (microns) | Density (g/cm$^3$) | Stiffness (gram-force) | Opacity (%) |
|---|---|---|---|---|---|---|
| No Binder | 47 B | 0 C | 129 C | 0.37 AB | 87 A | 72 A |
| Acrylic | 55 A | 15 BC | 141 BC | 0.39 A | 47 B | 66 B |
| Emulsion 13 | 53 A | 10 B | 157 A | 0.34 B | 84 A | 73 A |
| Dispersion #1 | 53 A | 11 AB | 146 AB | 0.36 AB | 104 A | 70 A |
| Dispersion #2 | 56 A | 15 A | 151 AB | 0.37 AB | 93 A | 72 A |
| Dispersion #3 | 55 A | 15 A | 158 B | 0.35 B | 99 A | 72 A |

|  | Tear (gram-force) | Burst (psig) | Tensile (dry) (kg/15 mm) | Tensile (Wet) (g/15 mm) | Abrasion (strokes) | Porosity (Coresta Units) |
|---|---|---|---|---|---|---|
| No Binder | 55 A | 21 B | 3.4 BC | 135 D | 1 A | 257 A |
| Acrylic | 53 A | 40 A | 4.1 AB | 531 A | 1.5 A | 263 A |
| Emulsion 13 | 55 A | 27 AB | 3.1 C | 188 CD | 1.5 A | 226 A |
| Dispersion #1 | 45 A | 37 A | 3.7 ABC | 375 B | 2 A | 227 A |
| Dispersion #2 | 53 A | 32 AB | 4.3 AB | 375 B | 1.5 A | 232 A |
| Dispersion #3 | 43 A | 38 A | 4.4 A | 338 BC | 1.75 A | 232 A |

|  | Minimum Pore Size (microns) | Maximum Pore Size (microns) | Mean Flow Pore Size (microns) | Oil Grease Resistance (Kit #) | Fold Endurance (# of Fold Cycles) |
|---|---|---|---|---|---|
| No Binder | 7.4 A | 17.9 A | 10.4 A | <1 A | 202 B |
| Acrylic | 8.1 A | 18.8 A | 11.2 A | <1 A | 1825 A |
| Emulsion 13 | 8.3 A | 19.4 A | 11.4 A | <1 A | 140 B |
| Dispersion #1 | 8.4 A | 18.2 A | 12.1 A | <1 A | 273 B |
| Dispersion #2 | 8.1 A | 19.3 A | 11.7 A | <1 A | 99 B |
| Dispersion #3 | 7.9 A | 18.5 A | 11.4 A | <1 A | 131 B |

Means within a column not sharing an uppercase letter are significantly different (P < 0.05).

TABLE 7

Calendered Cellulosic Hand Sheet with AKD & Clay Testing Results

|  | Final Binder Weight (g/m²) | % Binder (% w/w) | Thickness (microns) | Density (g/cm³) | Opacity (%) | Brightness (%) |
|---|---|---|---|---|---|---|
| No Binder | 50 | 0 | 74 C | 0.68 A | 74 BC | 73 A |
| Acrylic | 54 | 7 | 81 AB | 0.67 A | 75 AB | 73 A |
| Emulsion 13 | 54 | 7 | 85 A | 0.64 A | 76 A | 73 A |
| Dispersion #1 | 49 | 7 | 74 C | 0.65 A | 72 CD | 71 B |
| Dispersion #2 | 49 | 7 | 72 C | 0.68 A | 72 D | 71 B |
| Dispersion #3 | 49 | 8 | 76 BC | 0.64 A | 72 CD | 71 B |

|  | Gloss Front/60 (%) | Gloss Back/60 (%) | Gloss Front/20 (%) | Gloss Back/20 (%) | Fold Endurance (# of Fold Cycles) |
|---|---|---|---|---|---|
| No Binder | 7.7 B | 7.6 B | 2.0 B | 1.9 B | 183.7 A |
| Acrylic | 9.1 A | 8.8 A | 2.1 A | 2.1 A | 180.3 A |
| Emulsion 13 | 5.6 D | 5.5 E | 1.7 C | 1.7 C | 163.3 A |
| Dispersion #1 | 7.5 B | 7.1 BC | 1.8 C | 1.8 C | 50.0 A |
| Dispersion #2 | 6.7 C | 6.6 CD | 1.7 C | 1.7 C | 54.5 A |
| Dispersion #3 | 6.4 C | 6.3 D | 1.7 C | 1.7 C | 52.0 A |

Means within a column not sharing an uppercase letter are significantly different ($P < 0.05$).

11. Preparation and Testing of a Paint Composition

Dispersions #1-3 and Example 13 emulsion were mixed with 10% by weight rutile titanium dioxide (Nubiola). The dispersions were mixed together in a blender to form a binder. The resulting paint formulation was applied to washed 5 by 7 inch pieces of 10 mil aluminum sheet material. The coatings on the sheet material were formed using an Accu-Lab Drawdown Machine that was equipped with a number 32 and number 36 drawn down rod. The number 32 rod was used to form a 0.032 inch wet paint coating thickness. The number 36 rod was used to form a 0.036 inch wet paint coating thickness. Using the same coating technique and sheet material, painted samples of a commercial paint formulation (acrylic latex paint from Valspar, Inc. of Minneapolis, Minn.) were also prepared for comparative testing purposes. After allowing to dry for 6-7 hours, various properties of the samples was measured. The results are presented in Table 8.

TABLE 8

Paint Testing Results

|  | GSM (g/m²) | Thickness (microns) | Density (g/cc) | Flexibility/ Stiffness (mg/in²) | Thickness (dry film) (microns) | GSM (dry film) (g/m²) |
|---|---|---|---|---|---|---|
| Valspar | 479 A | 302 A | 1.63 A | 178 A | 61 A | 63 |
| Emulsion 13 | 277 C | 289 A | 1.01 A | 192 A | 58 A | 43 |
| Dispersion #1 | 242 C | 193 A | 1.26 A | 13 B | 30 B | 32 |
| Dispersion #2 | 393 B | 278 A | 1.43 A | 13 B | 54 A | 46 |
| Dispersion #3 | 393 B | 258 A | 1.55 A | 25 B | 54 A | 55 |

|  | Opacity (%) | Scratch resistance (g) | Cohesion (g) | Scrape resistance (g) | Gloss @ 60 (%) | Brightness (%) |
|---|---|---|---|---|---|---|
| Valspar | 106.9 A | 100 A | 1.3 B | 100 A | 10 D | 92 A |
| Emulsion 13 | 77.5 B | 125 A | 4.5 A | 88 AB | 6 E | 66 B |
| Dispersion #1 | 72.4 B | 38 A | 0.5 B | 25 C | 74 A | 67 B |
| Dispersion #2 | 78.6 B | 63 A | 0.5 B | 38 BC | 44 B | 66 B |
| Dispersion #3 | 74.6 B | 75 A | 0.5 B | 38 BC | 28 C | 63 C |

|  | Shore Hardness-D (g) |
|---|---|
| Valspar | 20 |
| Emulsion 13 | 25 |
| Dispersion #1 | 5 |
| Dispersion #2 | 5 |
| Dispersion #3 | 10 |

|  | GSM (g/m²) | Thickness (microns) | Density (g/cc) | Flexibility/ Stiffness (mg/in²) | Thickness (dry film) (microns) | GSM (dry film) (g/m²) |
|---|---|---|---|---|---|---|
| Valspar | 862 A | 503 A | 1.72 A | 650 A | 48 A | 48 |
| Emulsion 13 | 494 C | 419 A | 1.18 B | 377 B | 41 A | 25 |

TABLE 8-continued

Paint Testing Results

| | | | | | | |
|---|---|---|---|---|---|---|
| Dispersion #1 | 482 C | 280 B | 1.72 A | 14 C | 16 B | 15 |
| Dispersion #2 | 699 B | 518 A | 1.35 B | 19 C | 40 A | 38 |
| Dispersion #3 | 708 B | 493 A | 1.44 B | 48 C | 47 A | 42 |

| | Opacity (%) | Scratch resistance (g) | Cohesion (g) | Scrape resistance (g) | Gloss @ 60 (%) | Brightness (%) |
|---|---|---|---|---|---|---|
| Valspar | 102.7 A | 63 A | 0.5 B | 75 A | 10 D | 90 A |
| Emulsion 13 | 67.2 B | 88 A | 3.8 A | 75 A | 6 E | 64 B |
| Dispersion #1 | 66.0 B | 50 A | 0.5 B | 25 A | 81 A | 64 BC |
| Dispersion #2 | 67.8 B | 50 A | 0.5 B | 25 A | 79 B | 65 B |
| Dispersion #3 | 67.4 B | 75 A | 0.5 B | 60 A | 31 C | 62 C |

Means within a column not sharing an uppercase letter are significantly different ($P < 0.05$).

A number of embodiments have been described but a person of skill understands that still other embodiments are encompassed by this disclosure. It will be appreciated by those skilled in the art that changes could be made to the embodiments described above without departing from the broad inventive concepts thereof. It is understood, therefore, that this disclosure and the inventive concepts are not limited to the particular embodiments disclosed, but are intended to cover modifications within the spirit and scope of the inventive concepts including as defined in the appended claims. Accordingly, the foregoing description of various embodiments does not necessarily imply exclusion. For example, "some" embodiments or "other" embodiments may include all or part of "some", "other," "further," and "certain" embodiments within the scope of this invention.

For example, compositions, methods and applications within the scope of the disclosure can also be defined in accordance with the below embodiments.

1. A composition, comprising: a solid portion comprising an amount of an aqueous-alcohol soluble protein, and a liquid portion comprising an amount of water and an amount of acid, wherein the composition may form a dispersion of the solid portion in the liquid portion without the benefit of an alcohol.

2. A composition according to embodiment 1, wherein the water is distilled water.

3. A composition according to embodiments 1 or 2, wherein the amount of water is at least about 30%, at least about 35%, at least about 40%, at least about 45%, at least about 50%, at least about 55%, at least about 60%, at least about 65%, at least about 70%, at least about 75% by mass of the composition.

4. A composition according to embodiments 1 or 2, wherein the amount of water ranges from about 38.1% to about 99.6% by mass of the composition.

5. A composition according to any of embodiments 1-4, wherein the protein is chosen from proteins derived from milk, proteins derived from soy protein isolate, prolamins and combinations thereof.

6. A composition according to embodiment 5, wherein the protein derived from milk is casein, whey or combinations thereof.

7. A composition according to embodiment 5, wherein the protein is a prolamin.

8. A composition according to embodiment 7, wherein the prolamin is derived from corn, wheat gluten, barley, rye, sorghum, oats, and combinations thereof.

9. A composition according to embodiment 7, wherein the prolamin is chosen from zein, gliadin, glutenin, hordein, secalin, avenin, gluten, kafirin, and combinations thereof.

10. A composition according embodiment 9, wherein the prolamin is a zein.

11. A composition according to embodiment 10, wherein the zein is INVIZ™ V740 zein.

12. A composition according to embodiment 10, wherein the zein is derived from a corn ethanol fermentation process.

13. A composition according to embodiment 12, wherein the zein is derived from a corn ethanol process according to U.S. patent application Ser. No. 12/651,401.

14. A composition according to embodiment 10, wherein the zein is a zein composition according to U.S. patent application Ser. No. 12/965,255.

15. A composition according to embodiment 10, wherein the zein comprises at least one of beta zein, gamma zein, or combinations thereof.

16. A composition according to embodiment 15, wherein the zein comprises a total combined amount of beta zeins and gamma zeins of at least about 12% by mass of the zein.

17. A composition according to embodiment 16, wherein the total amount of beta zeins and gamma zeins is at least about 44% by mass of the zein.

18. A composition according to any of embodiments 10-17, wherein the amount of zein is at least about 10%, at least about 15%, at least about 20%, at least about 25%, at least about 30%, at least about 35% by mass of the composition.

19. A composition according to any of embodiments 10-17, wherein the amount of zein ranges from about 0.2% to about 34.6% by mass of the composition.

20. A composition according to embodiment 19, wherein the amount of zein ranges from about 2.2% to about 21.3% by mass of the composition.

21. A composition according to any of embodiments 1-20, wherein the acid is chosen from organic acids, inorganic acids and combinations thereof.

22. A composition according to embodiment 21, wherein the acid is chosen from water-soluble carboxylic acids, hydrochloric acid and combinations thereof.

23. A composition according to embodiment 22, wherein the carboxylic acids are chosen from: formic acid, acetic acid, propionic acid, succinic acid, glutaric acid, adipic acid, malic acid, citric acid, trans-aconitic acid, glycolic acid, levulinic acid, ascorbic acid, tartaric acid, and D-gluconic acid.

24. A composition according to any of embodiments 1-23, wherein the amount of acid is at least about 0.5%, at least about 1%, at least about 5%, at least about 10%, at least about 15%, at least about 20%, at least about 25%, at least about 30%, at least about 35%, at least about 40%, at least about 45% by mass of the composition.

25. A composition according to any of embodiments 1-23, wherein the amount of acid ranges from about 0.4% to about 48.1% by mass of the composition.

26. A composition according to embodiment 25, wherein the amount of acid ranges from about 16.3% to about 48.1% by weight of the composition.

27. A composition according to any of embodiments 1-26, wherein the composition further comprises an amount of an ester of a carboxylic acid.

28. A composition according to embodiment 27, wherein the ester of a carboxylic acid is chosen from methyl esters, ethyl esters, propyl esters, butyl esters of carboxylic acids and combinations thereof.

29. A composition according to embodiment 28, wherein the ester of a carboxylic acid is chosen from trimethyl citrate, dimethyl succinate, triethyl citrate, ethyl lactate, diethyl tartrate, tri-n-butyl citrate, dibutyl succinate, dibutyl sebacate, dibutyl tartrate, and combinations thereof.

30. A composition according to any of embodiments 27-29, wherein the amount of the ester ranges from about 0.3% to about 53.1% by mass of the composition.

31. A composition according to embodiment 30, wherein the amount of ester is at least about 0.5%, at least about 1.0%, at least about 1.5%, at least about 2.0%, at least about 2.5%, at least about 3.0%, or at least about 3.5% by mass of the composition.

32. A composition according to any of embodiments 1-31, wherein the solid component is dispersed in the liquid component.

33. A composition according to embodiment 32, wherein the solid component remains dispersed in the liquid component for at least about eight hours without stirring.

34. A composition according to any of embodiments 1-33, wherein the composition is a flowable composition.

35. A composition according to any of embodiments 1-34, wherein the composition is non-toxic.

36. A composition according to any of embodiments 1-34, wherein the composition comprises only food-grade materials.

37. A composition according to any of embodiments 1-34, wherein the composition comprises only pharmaceutically acceptable materials.

38. A composition according to any of embodiments 1-37 made by the process comprising combining the solid component, the liquid component, and an ester of a carboxylic acid, if present, to form a dispersion.

39. A composition according to claim 38, wherein combining comprises stirring.

40. A composition according to embodiment 38 or 39, wherein combining comprises heating.

41. A composition according to any of embodiments 1-39, wherein the amounts of protein, water, acid, and ester of carboxylic acid, if present, are chosen relative to one another to result in a flowable composition wherein the solid component is dispersible in the liquid component.

42. A composition according to embodiment 41, wherein the relative amounts of protein, water, acid and ester of carboxylic acid are chosen to maximize the amount of protein in the composition.

43. A composition made by a process, comprising: combining together an amount of water, an amount of acid, an amount of aqueous alcohol soluble protein, and optionally an amount of ester of a carboxylic acid to form a dispersion without the benefit of an alcohol.

44. A composition according to embodiment 43, wherein the protein is a prolamin.

45. A composition according to embodiment 43 or 44, wherein the dispersion is a flowable dispersion.

46. A composition according to any of embodiments 43-45, further comprising drying the dispersion.

47. A composition according to embodiment 46, wherein drying comprises lyophilizing or other suitable methods of drying.

48. A composition according to embodiments 46 or 47 further comprising re-dispersing the dried dispersion in water.

49. A composition according to any of embodiments 43-48, wherein the amounts of water, acid, protein, and ester, if present, are according to embodiments 3, 4, 18-20, 24-26, 30 and/or 31.

50. A composition according to any of embodiments 43-49, wherein the water may be distilled water, the protein may be according to any of embodiments 5-17, the acid may be according to any of embodiments 21-23, and/or the ester, if present may be according to any of embodiments 28 or 29.

51. A composition, comprising: a solid component comprising an aqueous alcohol soluble protein, and a liquid component comprising water and an acid, wherein the composition is alcohol-free.

52. A composition according to embodiment 51, wherein the solid component is dispersed in the liquid component.

53. A composition according to embodiment 51 or 52, wherein the amounts of water, acid, protein, and ester, if present, are according to embodiments 3, 4, 18-20, 24-26, 30 and/or 31.

54. A composition according to any of embodiments 51-53, wherein the water may be distilled water, the protein may be according to any of embodiments 5-17, the acid may be according to any of embodiments 21-23, and/or the ester, if present may be according to any of embodiments 28 or 29.

55. A composition according to any of embodiment 1-54 wherein the pH of the composition is less than about 8.

56. A composition according to embodiment 55, wherein the pH is about 7 or less.

57. A composition according to embodiment 56 wherein the composition is acidic.

58. A composition according to embodiment 57, wherein the pH is about 3 or less.

59. A composition according to embodiment 58, wherein the pH is about 2 or less.

60. An end use application produced from a composition according to any of embodiments 1-59, wherein the end use application is chosen from paints, binders, varnishes, coatings, inks, adhesives, and glues.

61. A binder produced from a composition according to any one of claims 1-59.

62. A binder according to embodiment 61, which is adapted for use in paper.

63. A coating produced from a composition according to any one of claims 1-59.

64. A coating according to embodiment 63, which is adapted for use in a product chosen from pharmaceuticals and paper.

65. A product chosen from paint, printing ink, varnish, adhesives, glues, binders, and food coating produced from a composition according to any one of embodiments 1-59.

66. A method, comprising: combining a set of ingredients in one or more steps to form a dispersion without the addition of alcohol, wherein the set of ingredients comprises an amount of an aqueous-alcohol soluble protein, an amount of water, an amount of an acid, and optionally an amount of an ester of a carboxylic acid.

67. A method according to embodiment 66, wherein combining comprises one or more stirring steps.

68. A method according to embodiments 66 or 67, wherein combining comprises one or more heating steps.

69. A method according to embodiment 66, wherein combining comprises: dissolving the acid in the water to form a first composition; and, mixing the ester and the protein into the first mixture to form a second composition.

70. A method according to embodiment 69, wherein combining further comprises heating and stirring the second composition until the second composition begins to reflux; and, cooling and stirring the second composition to about room temperature.

71. A method according to embodiment 66, wherein combining comprises: dissolving ester and acid in water to form a first liquid component; dissolving acid in water to form a second liquid component; adding the first liquid component to the protein to form a first mixture; stirring and heating the first mixture; heating the second liquid component; heating water; alternatively adding while stirring the heated second liquid component and the heated water in one or more steps to the first mixture to form a final mixture of desired viscosity; and, cooling while stirring the final mixture to room temperature.

72. A method according to any of embodiments 66-71, wherein the method further comprises drying the dispersion, for example freeze drying the dispersion, or drying the dispersion by any other suitable method.

73. A method according to embodiment 72, further comprising re-dispersing the dried, for example freeze-dried, dispersion in water.

74. A method according to any of embodiments 66-71, further comprising preparing paper using the dispersion as a binder.

75. A method according to any of embodiments 66-71, further comprising preparing paper using the dispersion as a coating.

76. A method according to any of embodiments 66-71, further comprising preparing a paint composition comprising the dispersion.

What is claimed is:

1. A method, comprising:
   combining a set of components in one or more steps to form a dispersion of an aqueous-alcohol soluble protein without the addition of alcohol, wherein the set of components comprises an amount of an aqueous-alcohol soluble protein, an amount of water, an amount of an acid, and an amount of an ester of a carboxylic acid, and further wherein combining comprises: dissolving the acid in water to form a first mixture; and, mixing the ester and the protein into the first mixture to form the dispersion.

2. A method according to claim 1, wherein mixing comprises stirring, heating, and cooling.

3. A method according to claim 1, further comprising: drying the dispersion.

4. A method according to claim 3, further comprising: re-dispersing the dried dispersion in water.

5. A method according to claim 1, further comprising preparing at least one of a binder or a coating from the dispersion.

6. A method according to claim 1, further comprising preparing a paint composition, a composition for use in pharmaceutical applications, a composition for use in food applications, a varnish composition, or an adhesive composition using the dispersion.

7. A method, comprising:
   combining a set of components in one or more steps to form a dispersion of an aqueous-alcohol soluble protein without the addition of alcohol, wherein the set of components comprises an amount of an aqueous-alcohol soluble protein, an amount of water, an amount of an acid, and an amount of an ester of a carboxylic acid, and further wherein combining comprises: dissolving ester and acid in water to form a first liquid portion; dissolving acid in water to form a second liquid portion; adding the first liquid portion to the protein to form a first mixture; stirring and heating the first mixture; heating the second liquid portion; heating water; alternatively adding while stirring the heated second liquid portion and the heated water in one or more steps to the first mixture to form a second mixture; and, cooling while stirring the second mixture to room temperature.

8. A method according to claim 7, further comprising: drying the dispersion.

9. A method according to claim 8, further comprising: re-dispersing the dried dispersion in water.

10. A method according to claim 7, further comprising preparing at least one of a binder or a coating from the dispersion.

11. A method according to claim 7, further comprising preparing a paint composition, a composition for use in pharmaceutical applications, a composition for use in food applications, a varnish composition, or an adhesive composition using the dispersion.

* * * * *